United States Patent
Adam et al.

(10) Patent No.: US 12,109,141 B2
(45) Date of Patent: Oct. 8, 2024

(54) NASAL SHAPER

(71) Applicants: DOLIAM INVEST, Maisons-Laffitte (FR); ASSISTANCE PUBLIQUE—HOPITAUX DE PARIS, Paris (FR)

(72) Inventors: Jeremy Adam, Paris (FR); Benoit Perrin, Clamart (FR); Roman Hossein Khonsari, Paris (FR)

(73) Assignees: DOLIUM INVEST (FR); ASSISTANCE PUBLIQUE—HOPITAUX DE PARIS (FR)

( * ) Notice: Subject to any disclaimer, the term of this patent is extended or adjusted under 35 U.S.C. 154(b) by 397 days.

(21) Appl. No.: 17/276,397

(22) PCT Filed: Sep. 27, 2019

(86) PCT No.: PCT/EP2019/076319
§ 371 (c)(1),
(2) Date: Mar. 15, 2021

(87) PCT Pub. No.: WO2020/070028
PCT Pub. Date: Apr. 9, 2020

(65) Prior Publication Data
US 2022/0039993 A1     Feb. 10, 2022

(30) Foreign Application Priority Data
Oct. 1, 2018   (FR) ...................................... 18/59085

(51) Int. Cl.
*A61F 5/08*          (2006.01)

(52) U.S. Cl.
CPC ..................................... *A61F 5/08* (2013.01)

(58) Field of Classification Search
CPC .. A61F 5/08; A61F 5/56; A61F 5/566; A61M 15/08; A61M 16/0666; A62B 23/06
See application file for complete search history.

(56) References Cited

U.S. PATENT DOCUMENTS

| 5,665,104 A | 9/1997 | Lee |
| 2004/0089303 A1 | 5/2004 | Chien |
| (Continued) | | |

FOREIGN PATENT DOCUMENTS

| EP | 1917993 A1 | 5/2008 |
| JP | H10323362 A | 12/1998 |
| (Continued) | | |

OTHER PUBLICATIONS

International Search Report; PCT Application No. PCT/EP2019/076319; Dated Nov. 22, 2019, 2 pages.
(Continued)

*Primary Examiner* — Majid Jamialahmadi
(74) *Attorney, Agent, or Firm* — Dilworth IP, LLC

(57) ABSTRACT

A nasal shaper configured to be introduced into a nose of a subject, the nasal shaper including two tubes suitable for each being introduced into a nostril of the nose, connected together at their lower ends by a connecting bridge and a plate attached to the connecting bridge and extending opposite the connecting bridge relative to the tubes, the plate being configured to exert a pressure on the philtrum of the subject when the tubes are each introduced into a nostril of the nose.

19 Claims, 3 Drawing Sheets

(56) References Cited

U.S. PATENT DOCUMENTS

| | | | | |
|---|---|---|---|---|
| 2006/0085027 A1* | 4/2006 | Santin | ............... | A61F 5/56 |
| | | | | 606/199 |
| 2009/0054923 A1* | 2/2009 | Benson | ............... | A61F 5/08 |
| | | | | 606/199 |
| 2014/0326244 A1* | 11/2014 | Orts Paya | ............... | A61F 5/08 |
| | | | | 606/199 |
| 2016/0153214 A1* | 6/2016 | Castro | ............... | E05B 67/003 |
| | | | | 70/49 |
| 2018/0153728 A1* | 6/2018 | Le | ............... | A61F 5/08 |

FOREIGN PATENT DOCUMENTS

| | | |
|---|---|---|
| JP | 2007195604 A | 8/2007 |
| RU | 2477088 C1 | 3/2013 |
| WO | 2017020068 A1 | 2/2017 |

OTHER PUBLICATIONS

Notice of Reasons for Refusal in JP Patent Application No. 2021-542270 dated Aug. 30, 2023.

* cited by examiner

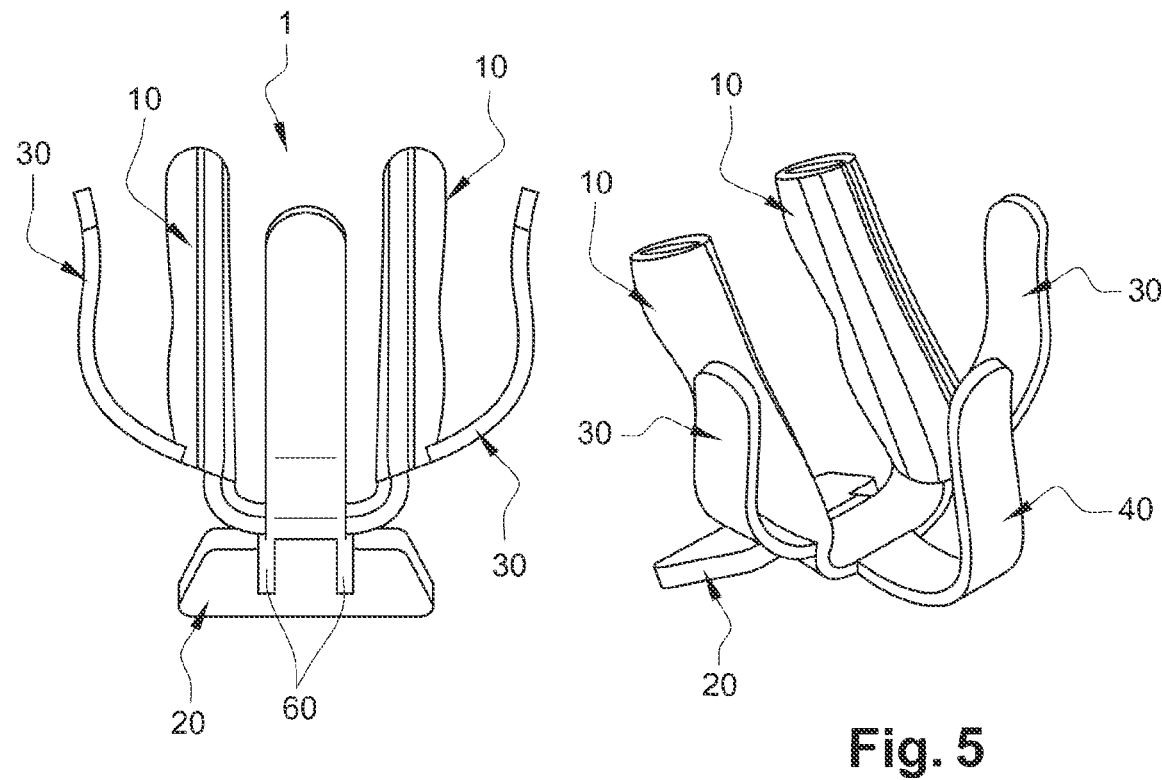
Fig. 4
Fig. 5
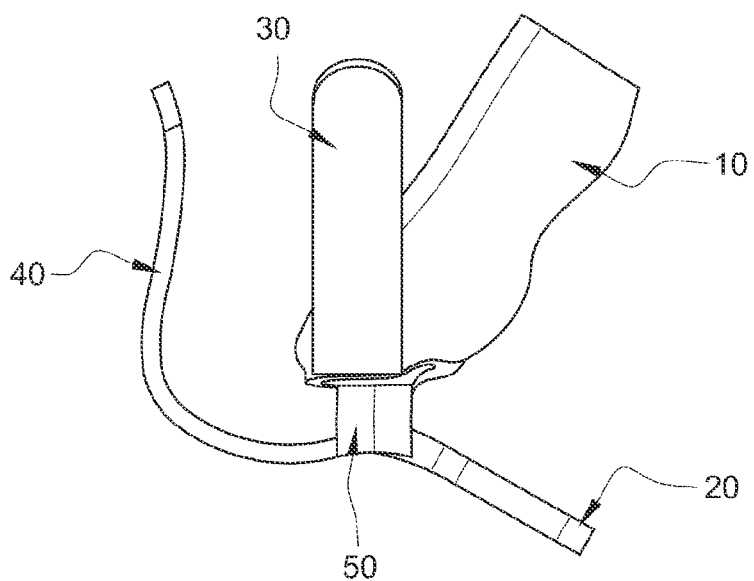
Fig. 6

NASAL SHAPER

FIELD OF THE INVENTION

The invention relates to a nasal shaper, intended to shape the nostrils, especially after rhinoplasty treatment.

BACKGROUND OF THE INVENTION

Nasal shapers, such as for example that described in patent RU 2 477 088, used after rhinoplasty, and in particular in case of cleft lip and cleft palate reconstructive surgery in the child, are already known. These shapers function in a relatively satisfactory way. It is also known that any scar may have an unaesthetic appearance due to the bulges or hollows created during healing. This is a particular problem for a scar on the face, placed in the area extending between the lip and the nose, i.e. in the area of the philtrum.

However, the nasal shaper described in patent RU 2 477 088 is unable to obtain in all patients a scar of satisfactory aesthetic appearance.

The invention aims in particular to provide a nasal shaper which improves the healing after rhinoplasty, while guaranteeing the restoration of nasal breathing and fighting against the creation of oedemas.

Thus, the invention relates to a nasal shaper configured to be introduced into the nose of a subject and comprising
  two tubes suitable for each being introduced into a nostril of the nose, connected together at their lower ends by a connecting bridge and
  a plate attached to the connecting bridge and extending opposite the connecting bridge relative to the tubes, the plate being configured to exert a pressure on the philtrum of the subject when the tubes are each introduced into a nostril of the nose.

Thus, a nasal shaper is proposed which comprises a plate designed to press on the philtrum after the shaper has been positioned in the nostrils. Due to this pressure exerted on the philtrum, the plate not only protects a scar on the philtrum, but can also exert sufficient pressure on the scar to avoid a bulging or hollow scar. The action of this plate therefore obeys the principle of pressotherapy, which has recognised benefits on surgical scars.

Note that the shaper is particularly interesting due to this aspect of pressure on the scar: not only is the scar protected, but pressure is applied to control the healing process. We therefore understand that the plate proposed is configured to be in contact with the surface of the philtrum.

In this case, "lower end" of the tubes means the end which is located at the lower end of the nostrils when the shaper is in position, The nasal shaper may further comprise the following characteristics, taken alone or in combination:
  The plate is attached to the connecting bridge, being deformable between:
    a rest position, in which the plate extends towards the rear of the nasal shaper, opposite the tubes before positioning the shaper, and
    a use position, when the nasal shaper is introduced into the nose, in which the plate extends towards the front of the nasal shaper,
  This configuration of the plate movable between two positions is particularly advantageous to exert a pressure on the philtrum,
  The nasal shaper comprises stiffening means, exerting a force to return the plate to its rest position, for example an insert. The stiffening means may be made in one piece with the plate or attached to the plate. In addition, they may be made of the same material as the plate or of a different material. Such stiffening means further improve the pressure exerted by the plate on the philtrum, by increasing the force exerted to return the plate to its rest position.
  Each tube comprises in its upper front part at least one protuberance to position the tube in the nostril. The one or more protuberances are thus positioned in the upper front end of the nostril, to hold the shaper more securely.
  Each tube comprises in its rear part at least one blocking protuberance to block the tube in the nasal cavities of the subject, and preferably two blocking protuberances in the nasal cavities of the subject. This embodiment is particularly advantageous. Thus, we understand that when the shaper is in position in the nostrils, the protuberance is positioned under the concha, for optimum positioning and holding of the shaper. It has been observed that on the existing shapers, especially that proposed in publication RU2477088, which have a rear part with no such protuberance, the shaper does not remain correctly in position in the nostrils since it tends to slide downwards, which means that it often has to be sutured in the nose of the subject, more especially for a child. We understand that the protuberance corresponds to a convex part, projecting from the rear surface of the tube. When the tube comprises two protuberances, it comprises in fact two convex parts separated by a concave part,
  The lower end of each tube has a recess so as to leave a space between the lower end of the tube and the bottom of the nostril; preferably, this recess has the general shape of a step, provided with fillets to soften the corners, connecting the rear and the lower part of the tube. We thus obtain a shape with no sharp corners, which avoids rubbing on the stitches made at the entrance of the nostrils, which may be painful and/or damage the stitches.
  The nasal shaper further comprises external tabs to hold the shaper on the nose, extending upwards from the lower end of the tubes, preferably two lateral tabs intended to press against the wings of the nose and/or one front tab intended to press against the tip of the nose. The presence of these tabs allows the nasal shaper to be held more securely in the nose, and may advantageously enable a pressure to be applied on the various tissue layers of the nasal wings, which may be separated during an operation, thereby improving the healing and making it possible to keep the shape required by a surgeon during the operation. These tabs may also be used to support stitches made through the alas, improving even further the contact between the various tissue layers of the nasal wings.
  The nasal shaper comprises silicone, it is preferably made of silicone.
  The plate and/or the stiffening elements are made of a material which is stiffer than the material of the tubes.
  The nasal shaper comprises materials of different colours. Thus, the shaper can be made in colours best corresponding to the patient's skin colour, decorations may also be made on the shaper.
  The nasal shaper has a connecting bridge, or columella, of variable length. Due to the variable length of its connecting bridge, the nasal shaper can adapt to anatomic differences, for example ethnic differences, in humans.

The invention also relates to a nasal shaper comprising two tubes suitable for each being introduced into a nostril of the nose, connected together at their lower ends by a connecting bridge, each tube comprising in its rear part at least one blocking protuberance to block the tube in the nasal cavities of the subject, preferably two blocking protuberances in the nasal cavities of the subject.

As described above, we understand that such a nasal shaper solves the problem of holding the shaper more securely in the nostril, since due to the one or more protuberances, there is no need to suture the shaper in the nostril to hold it. Such a nasal shaper may comprise one or more of the characteristics of the nasal shaper described above, taken alone or in combination. We understand in particular that the nasal shaper may comprise, or not, the plate attached to the connecting bridge.

Another object of the invention is a method for manufacturing one as described above, comprising an injection moulding step, and the mould preferably being manufactured by additive synthesis.

Additive synthesis can be used advantageously to manufacture a customised mould, therefore a customised nasal shaper, which is particularly interesting to guarantee that the shaper is held securely and that correct pressure is applied on the philtrum.

BRIEF DESCRIPTION OF THE FIGURES

The invention will be better understood on reading the following description, given solely by way of example and with reference to the accompanying drawings in which:

FIG. 4 is a front view of a nasal shaper according to a second embodiment of the invention, FIG. 5 is a perspective view of the nasal shaper of FIG. 2, FIG. 6 is a side view of the nasal shaper of FIG. 2.

DETAILED DESCRIPTION

Figure 1:
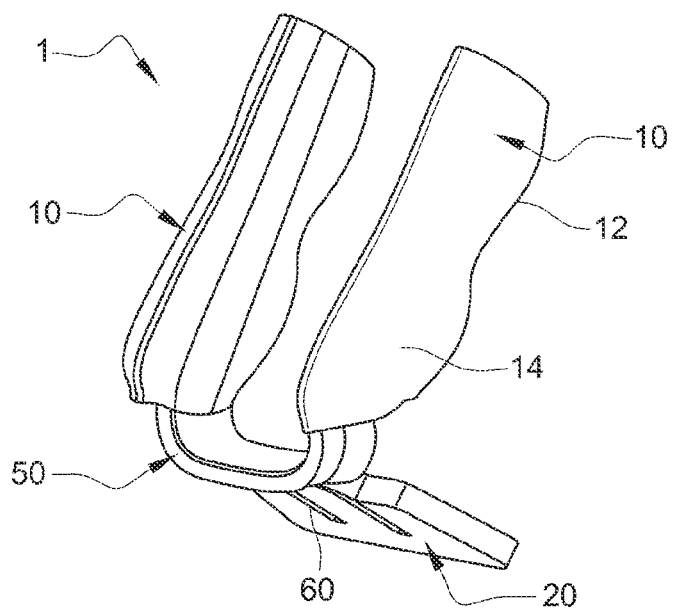
FIG. 1 is an isometric perspective view of a nasal shaper according to a first embodiment of the invention.
Figure 2:
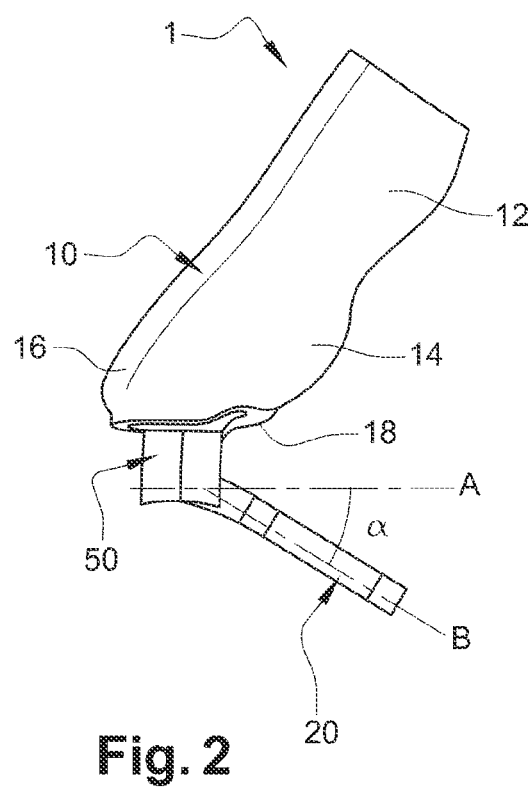
FIG. 2 is a side view of the nasal shaper of FIG. 1.
Figure 3:
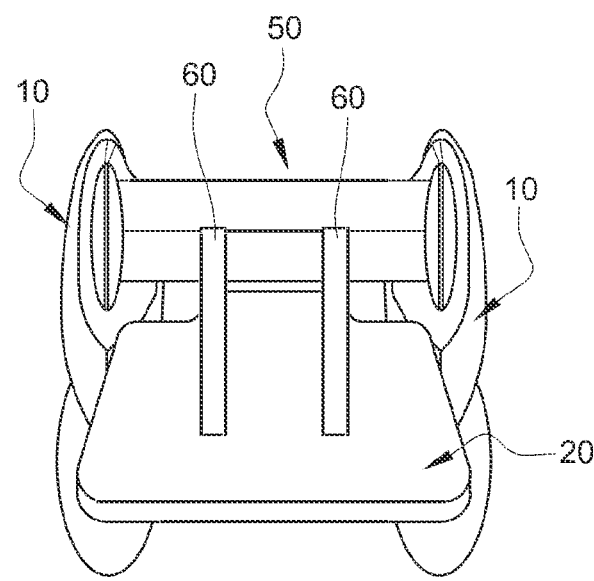
FIG. 3 is a bottom view of the nasal shaper of FIG. 1.

FIGS. 1 to 3 show a nasal shaper according to a first embodiment of the invention, designated by the general reference 1.

Such nasal shapers are generally used after rhinoplasty. A nasal shaper 1 is used most frequently after cleft lip and cleft palate reconstructive surgery in a child. After this type of surgery, the nasal shaper is used to shape the nostrils of the subject, according to a shape predefined by the surgeon, while allowing the subject to breathe, and also, especially in an infant, to feed being able to suck easily. In addition, as detailed below, and according to the principle of pressotherapy, this nasal shaper offers the advantage of obtaining a scar with a better appearance than those obtained with shapers of the state of the art.

The nasal shaper 1 shown on FIGS. 1 to 3 comprises two tubes 10 intended to be introduced into the nostrils of a subject. The tubes 10 are connected together by a connecting bridge 50. When the tubes 10 are in position in the nostrils of the subject, the connecting bridge 50 is generally substantially in contact with the base of the nose of the subject.

In the embodiment shown on FIGS. 1 to 3, the nasal shaper 1 further comprises a plate 20 which is attached to the connecting bridge 50. The plate 20 is configured so that, when the nasal shaper 1 is in position in the nose of a subject, i.e. when the tubes 10 are each introduced into a nostril of the subject, the plate 20 is positioned flat on the philtrum of the subject, and exerts a pressure on the philtrum. This pressure helps to obtain a scar on the philtrum of satisfactory aesthetic appearance.

Advantageously, the plate 20 is movable between a rest position and a use position. In its rest position, the plate 20 extends towards the rear of the nasal shaper 1, opposite the tubes 10. This rest position of the plate 20 is generally the position of the plate 20 obtained after manufacturing the nasal shaper. The angle α formed by the plane of the plate and the plane passing though the lower part of the connecting bridge 50, shown on FIG. 2, is between 0° and 90°.

When the plate 20 is in the use position, which corresponds to the position in which the nasal shaper 1 is in position in the nose of the subject, the plate 20 extends towards the front of the nasal shaper 1, opposite the tubes 10 relative to the connecting bridge 50, The plate 20 is configured such that when the nasal shaper 1 is positioned on the nose of the subject, the plate exerts a pressure considered to be sufficient to improve healing.

Advantageously, as shown on FIG. 3, the nasal shaper 1 comprises stiffening means 60 which increase the force used to return the plate 20 from its use position to its rest position. These stiffening means 60 may be inserts placed in the lower part of the plate 20 and of the connecting bridge 50, or be made in one piece with the rest of the plate 20. These stiffening means 60 may form, at least partly, the elements attaching the plate 20 to the connecting bridge 50. The presence of these stiffening means 60 improves the action of the plate 20 by increasing the pressure it exerts on the philtrum of the subject.

In one embodiment, the tubes 10 of the nasal shaper 1 comprise a protuberance 16, shown on FIG. 2, located in the front and upper part of the tube 10 and intended to be positioned in the front and upper part of a nostril, which offers the advantage of holding the nasal shaper 1 more securely in the nose of the subject.

In another embodiment, each of the tubes 10 is provided with at least one blocking protuberance 12, 14 as shown in particular on FIGS. 1 and 2, and positioned in the rear part of the tube. These blocking protuberances are positioned in the nasal cavities of the subject when the nasal shaper is in position, and more precisely under the concha. The presence of these blocking protuberances 12, 14 allows optimum positioning and holding of the nasal shaper. This may in particular avoid the need for suturing the nasal shaper in the nose of the subject, which was a frequent and major disadvantage of the existing shapers.

In yet another embodiment, each tube 10 is provided at its lower front end with a recess 18, shown on FIG. 2, so as to leave a space between the lower end of the tube 10 and the bottom of the nostril. Advantageously, this recess has the general shape of a step, provided with fillets to soften the corners. In other words, the recess has a substantially "S-shaped" section, the ends of the S being tangential respectively to the tube 10 and the connecting bridge 50.

In another embodiment shown on FIGS. 4 to 6, the nasal shaper 1 further comprises external holding tabs 30, 40, intended to hold the nasal shaper 1 in position in the nose of the subject. These tabs 30, 40 extend upwards from the lower ends of the tubes 10. These tabs may be two external lateral tabs 30 each intended to press on one side of the wings of the nose. A front tab 40 intended to press on the tip of the nose may also be used. These lateral 30 and front 40 tabs can be used alone or in combination.

Apart from holding the nasal shaper 1 more securely in the nose of the subject, these tabs enable a pressure to be applied on the various tissue layers of the nasal wings, which are generally separated during surgery. This improves the healing and makes it possible to keep the shape given to the nostrils by the surgeon during the operation. Lastly, these tabs may also be used to support stitches made through the alas, improving even further the contact between the various tissue layers of the nasal wings.

After cleft lip and cleft palate reconstructive surgery, the surgeon advantageously uses, during the next few days, a nasal shaper 1 not comprising the tabs 30, 40, then during the next few weeks, a nasal shaper 1 with the external lateral tabs 30 and/or the front external tab 40, The nostrils therefore heal better and can be shaped as required.

In another embodiment, the length of the connecting bridge 50 is variable and can be adapted to the anatomy of each subject.

Preferably, the tubes 10 are made of a flexible material, so that they can be introduced into the nostril more easily and are less uncomfortable for the subject. Silicone is a material which is especially suitable for the tubes 10. It is in fact highly flexible, biologically inert and well-tolerated by the body. Similarly, the connecting bridge 50 is preferably flexible, and silicone is especially suitable. Advantageously, the connecting bridge 50 is made in one piece with the tubes 10.

Preferably, the plate 20 also comprises silicone. In addition, the plate 20 is configured so that a sufficient and substantially uniform pressure can be applied on the philtrum, and more particularly on the area of the philtrum where the scar is located, having suitable, in other words relatively high, stiffness to do this.

Thus, advantageously, the plate 20 is stiffer than the tubes 10 and the connecting bridge 50. In order to make the tubes 10 easier to use and more comfortable, they should preferably be highly flexible. However, to operate satisfactorily, the plate 20 must be stiff.

The stiffening means 60 also advantageously comprise silicone, or are even made of silicone. Since they must help to increase the return force exerted on the plate 20, their stiffness is generally relatively high, for example the same as that of the plate 20. In one embodiment, the stiffening means 60 are made in one piece with the plate 20, and are attached to the connecting bridge 50. In another embodiment, the stiffening means 60 are inserts placed in the lower part of the plate 20, and connected to the connecting bridge 50.

Another object of the invention is a method for manufacturing the nasal shaper 1. Preferably, the nasal shaper 1 is manufactured by injection moulding. Advantageously, the material used is silicone.

In a particularly advantageous embodiment, the mould used for the injection moulding is itself manufactured by additive synthesis. This manufacturing method can optionally be used to manufacture customised moulds.

Figure 7:
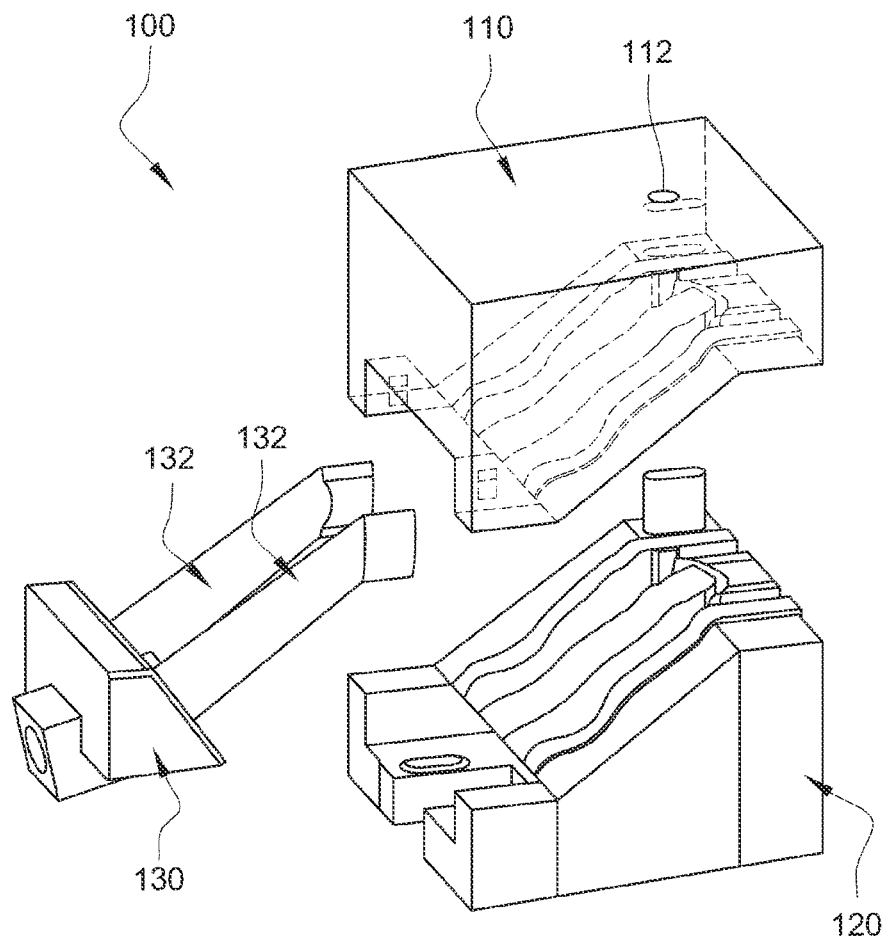
FIG. 7 is a perspective view of a mould to manufacture a nasal shaper similar to that of FIG. 1.

FIG. 7 shows an example of a mould used to manufacture the nasal shaper 1. The mould 100 comprises two external parts 110 and 120 and one internal part 130. The part 110 is the upper part, and comprises an orifice 112 to inject silicone (or other suitable material). The part 120 is the lower part of the mould. The mould 100 also comprises an internal part 130, comprising in particular two lugs 132 around which the tubes 10 of the nasal shaper 1 will be moulded.

TABLE 1

| | |
|---|---|
| 1 | Nasal shaper |
| 10 | Tube intended to be introduced into a nostril |
| 12 | Rear protuberance of the tube 10 intended to be received by a concha of the nose of a subject |
| 14 | Rear protuberance of the tube 10 intended to be received by a concha of the nose of a subject |
| 16 | Front protuberance of the tube 10 intended to be received by the upper front part of the nose of a subject |
| 18 | Recess at the lower end of the tube 10, with softened corner |
| 20 | Plate pressing on the philtrum |
| 30 | Lateral external tab |
| 40 | Front external tab |
| 50 | Connecting bridge between the tubes 10 |
| 60 | Stiffening means |
| 100 | Mould to manufacture the nasal shaper 1 |
| 110 | Upper part of the mould |
| 112 | Injection orifice |
| 120 | Lower part of the mould |
| 130 | Part of the mould intended to form the tubes 10 |
| 132 | Lugs |

The invention is not limited to the embodiments described and other embodiments will be clearly apparent to those skilled in the art.

In particular, the nasal shaper 1 could comprise no plate 20. In this case, the mere fact that the tubes are provided with one or two blocking protuberances 12, 14 provides a nasal shaper which can be held more securely in the nose, in particular a shaper which does not need to be sutured in the nose.

In other words, the nasal shaper 1 is configured to be introduced into the nose of a subject and comprises:
  two tubes 10 suitable for each being introduced into a nostril of the nose, connected together at their lower ends by a connecting bridge 50 and,
  wherein each tube 10 comprises in its rear part at least one blocking protuberance 12, 14 to block the tube 10 in the nasal cavities of the subject, preferably two blocking protuberances 12, 14 in the nasal cavities of the subject.

This type of nasal shaper is useful for example for rhinoplasties in which no stitches are made on the philtrum. When the shaper is in position in the nostrils, the protuberance is positioned under the concha, for optimum positioning and holding of the shaper. It has been observed, in fact, that on the existing shapers, especially that proposed in publication RU2477088; which are not provided with these protuberances, the shaper does not remain correctly in position in the nostrils since it tends to slide downwards, which means that it often has to be sutured in the nose.

In another embodiment, the nasal shaper 1 does not comprise a plate 20 but comprises external tabs to hold the shaper on the nose of the subject. In such an embodiment, the nasal shaper 1 is configured to be introduced into the nose of a subject and comprises:
  two tubes 10 suitable for each being introduced into a nostril of the nose, connected together at their lower ends by a connecting bridge 50 and
  external tabs 30, 40 to hold the shaper on the nose, extending upwards from the lower ends of the tubes, preferably two lateral tabs 30 intended to press against the wings of the nose and/or one front tab 40 intended to press against the tip of the nose.

This type of nasal shaper is useful for example for rhinoplasties in which no stitches are made on the philtrum. The presence of the tabs 30, 40 allows the shaper to be held more securely, and also enables a pressure to be applied on the various tissue layers of the nasal wings, if they are separated during surgery, thereby improving the healing and making it possible to keep the shape required by the surgeon during the operation. These tabs 30, 40 may also be used to support stitches made through the alas, improving even further the contact between the various tissue layers of the nasal wings.

In addition, the above two embodiments can be combined, an object of the invention in this case being a nasal shaper 1 comprising:

two tubes 10 suitable for each being introduced into a nostril of the nose, connected together at their lower ends by a connecting bridge 50 and, wherein each tube 10 comprises in its rear part at least one blocking protuberance 12, 14 to block the tube 10 in the nasal cavities of the subject, preferably two blocking protuberances 12, 14 in the nasal cavities of the subject.

external tabs 30, 40 to hold the shaper on the nose, extending upwards from the lower ends of the tubes, preferably two lateral tabs 30 intended to press against the wings of the nose and/or one front tab 40 intended to press against the tip of the nose.

Other combinations or deletions of characteristics of the various embodiments could be considered.

The invention claimed is:

1. A nasal shaper configured to be introduced into a nose of a subject, the nasal shaper comprising:

two tubes suitable for each being introduced into a nostril of the nose, connected together at their lower ends by a connecting bridge, and a plate attached to the connecting bridge and extending opposite the connecting bridge relative to the tubes, the plate being configured to exert a pressure on the a philtrum of the subject when the tubes are each introduced into the nostril of the nose, wherein the plate, attached to the connecting bridge, is deformable between a rest position, in which the plate extends towards a rear of the nasal shaper, opposite the tubes before positioning the shaper, and a use position, when the nasal shaper is introduced into the nose, in which the plate extends towards a front of the nasal shaper, the nasal shaper further comprising a stiffening element exerting a force to return the plate to the rest position.

2. The nasal shaper according to claim 1, wherein each of the tubes comprises in its upper front part at least one protuberance to position the respective one of the tubes in the nostril.

3. The nasal shaper according to claim 1, wherein each of the tubes comprises in its rear part at least one blocking protuberance to block the respective one of the tubes in the-nasal cavities of the subject.

4. The nasal shaper according to claim 1, wherein the lower end of each of the tubes has a recess so as to leave a space between the lower end of the tube and a bottom of the nostril.

5. The nasal shaper according to claim 4, wherein the recess has a general shape of a step, provided with fillets to soften corners, connecting a rear and the lower end of the tube.

6. The nasal shaper according to claim 1, further comprising external tabs to hold the shaper on the nose, extending upwards from the lower ends of the tubes.

7. The nasal shaper according to claim 6, wherein the external tabs include two lateral tabs intended to press against the wings of the nose or one front tab intended to press against a tip of the nose.

8. The nasal shaper according to claim 6, wherein the external tabs include two lateral tabs intended to press against wings of the nose and one front tab intended to press against a tip of the nose.

9. The nasal shaper according to claim 1, comprising silicone.

10. The nasal shaper according to claim 1, wherein the plate is made of a material which is stiffer than a material of the tubes.

11. The nasal shaper according to claim 1, wherein the stiffening element is made of a material which is stiffer than a material of the tubes.

12. The nasal shaper according to claim 1, comprising materials of different colors.

13. The nasal shaper according to claim 1, wherein the connecting bridge has a variable length.

14. The nasal shaper according to claim 1, wherein the stiffening element is an insert in the plate.

15. The nasal shaper according to claim 14, wherein the plate is attached to the connecting bridge at least partly by the stiffening element.

16. The nasal shaper according to claim 1, wherein each of the tubes comprises in its rear part two blocking protuberances to block the tube in nasal cavities of the subject.

17. The nasal shaper according to claim 1, wherein the nasal shaper is made of silicone.

18. The nasal shaper according to claim 1, wherein the stiffening element is formed as one piece with the plate.

19. The nasal shaper according to claim 18, wherein the plate is attached to the connecting bridge at least partly by the stiffening element.

\* \* \* \* \*